United States Patent [19]

Rasberger et al.

[11] 4,185,007

[45] Jan. 22, 1980

[54] BARBITURIC ACID DERIVATIVES CONTAINING A PHENOLIC MOIETY AND/OR A HINDERED AMINE MOIETY

[75] Inventors: Michael Rasberger, Riehen; Friedrich Karrer, Zofingen, both of Switzerland

[73] Assignee: Ciba-Geigy Corporation, Ardsley, N.Y.

[21] Appl. No.: 809,577

[22] Filed: Jun. 24, 1977

[30] Foreign Application Priority Data

Jul. 8, 1976 [CH] Switzerland .................. 8775/76

[51] Int. Cl.$^2$ .................. C07D 401/04; C07D 401/14; C08K 5/34
[52] U.S. Cl. .................. 260/45.8 N; 252/51.5 R; 544/301; 546/246

[58] Field of Search .................. 260/257, 45.8 N; 252/51.5 R; 544/301

[56] References Cited

U.S. PATENT DOCUMENTS

| | | | |
|---|---|---|---|
| 3,636,080 | 1/1972 | Brossi et al. | 260/257 |
| 3,930,006 | 12/1975 | Wiggins et al. | 424/274 |
| 4,028,334 | 6/1977 | Chalmers | 260/45.8 N |

FOREIGN PATENT DOCUMENTS

76/88484  8/1976  Japan.

Primary Examiner—Mark L. Berch
Attorney, Agent, or Firm—Wenderoth, Lind & Ponack

[57] ABSTRACT

New barbituric acid derivatives containing at least one phenolic moiety and at least one hindered amine moiety are effective lightstabilizers and antioxidants.

10 Claims, No Drawings

BARBITURIC ACID DERIVATIVES CONTAINING A PHENOLIC MOIETY AND/OR A HINDERED AMINE MOIETY

The present invention relates to new piperidine derivatives of barbituric acid, their manufacture, their use for stabilising organic material and to the organic material protected, with the aid thereof, against oxidative and light-induced degradation.

The use of piperidine derivatives of 1.3-pyrimidine and 1,3,5-triazine as a light stabiliser is known from British Patent Specification No. 1,393,551. Furthermore, phenolic derivatives of barbituric acid, which are suitable for use as antioxidants, are known from DT-OS No. 2,025,860.

A class of piperidine derivatives of barbituric acid, which is distinguished by good light-stabilising and antioxidative properties, has now been found.

The new compounds correspond to the general formula

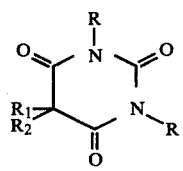

in which R is hydrogen or one of the groups

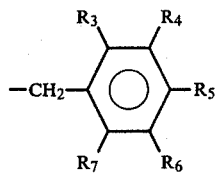

or

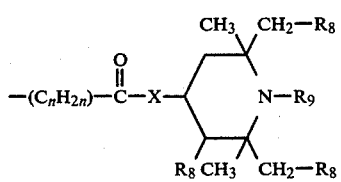

or an addition salt thereof, wherein one of $R_3$ and $R_5$ is —OH and the other is hydrogen, $R_4$ denotes $C_1-C_{12}$ alkyl, $C_5-C_7$ cycloalkyl, $C_6-C_{10}$ aryl or $C_7-C_9$ aralkyl, $R_6$ and $R_7$ are hydrogen, $C_1-C_{12}$ alkyl, $C_5-C_7$ cycloalkyl, $C_6-C_{10}$ aryl or $C_7-C_9$ aralkyl, $R_8$ is hydrogen or $C_1-C_8$ alkyl and $R_9$ is hydrogen, oxyl, $C_1-C_{12}$ alkyl, $C_3-C_6$ alkenyl, $C_3-C_4$ alkinyl, $C_2-C_{21}$ alkoxyalkyl, $C_7-C_8$ aralkyl, 2,3-epoxypropyl, an aliphatic acyl group with 1-4 C atoms or one of the groups —$CH_2COOR_{10}$, —$CH_2$—$CH(R_{11})$—$OR_{12}$, —$COOR_{13}$ or —$CONHR_{13}$, wherein $R_{10}$ is $C_1-C_{14}$ alkyl, $C_3-C_6$ alkenyl, phenyl, $C_7-C_8$ aralkyl or cyclohexyl, $R_{11}$ is hydrogen, methyl or phenyl, $R_{12}$ denotes hydrogen, an aliphatic, aromatic, araliphatic or alicyclic acyl group with 1-18 C atoms, wherein the aromatic part, if appropriate, can be substituted by chlorine, $C_1-C_4$ alkyl, $C_1-C_8$ alkoxy and/or by hyroxyl, and $R_{13}$ denotes $C_1-C_{12}$ alkyl, cyclohexyl, phenyl or benzyl, and X is is —O— or —$NR_{14}$— wherein $R_{14}$ denotes hydrogen or $C_1-C_{12}$ alkyl, n denotes 1 to 5 and, if R is hydrogen or a group of the formula II, $R_1$ denotes hydrogen, $C_1-C_{18}$ alkyl, $C_5-C_7$ cycloalkyl, a group of the formula II or a group of the formula $R_{15}$—CO—$(C_nH_{2n})$—(IV) wherein $R_{15}$ denotes $C_1-C_{18}$ alkyl, $C_5-C_7$ cycloalkyl, $C_1-C_{18}$ alkoxy, $C_5-C_7$ cycloalkoxy, $C_7-C_9$ aralkyl or a group of the formula

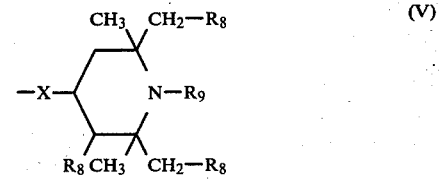

or an addition salt thereof, wherein $R_8$ and $R_9$ have the meaning defined above, and, if R is a group of the formula III, $R_1$ denotes hydrogen or a group of the formula II and, if R is hydrogen or a group of the formula II, $R_2$ denotes a group of the formula III or VI

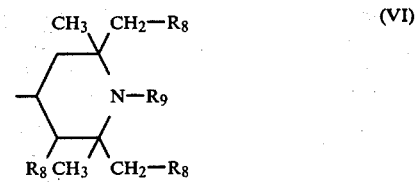

and, if R is a group of the formula III, $R_2$ denotes hydrogen, $C_1-C_{18}$ alkyl, $C_5-C_7$ cycloalkyl, $C_6-C_{10}$ aryl, $C_7-C_9$ aralkyl or one of the groups II, III or V.

As branched or unbranched $C_1-C_{12}$ alkyl, $R_4$, $R_6$ and $R_7$ can be, for example, methyl, ethyl, isopropyl, sec.-butyl, tert.-buty, amyl, n-hexyl, 1,1,3,3-tetramethylbutyl, tert.-nonyl, n-decyl or n-dodecyl. Alkyl groups with 1-8 C atoms and especially those with 1-4 C atoms are preferred as $R_4$ and $R_6$. Alkyl groups with 1-6 C atoms and especially methyl are preferred as $R_7$.

Examples of $R_4$, $R_6$ and $R_7$ as $C_5-C_7$ cycloalkyl are cyclopentyl, methylcyclopentyl, cyclohexyl or methylcyclohexyl.

Examples of $R_4$, $R_6$ and $R_7$ as $C_6-C_{10}$ aryl are phenyl, α-naphthyl or β-naphthyl, especially phenyl.

Examples of $R_4$, $R_6$ and $R_7$ as $C_7-C_9$ aralkyl are benzyl, α,α-dimethylbenzyl, α-phenylethyl or 2-phenylpropyl, especially benzyl.

Examples of $R_8$ as $C_1-C_{12}$ alkyl are methyl, ethyl, n-butyl, n-hexyl, n-octyl, n-decyl or n-dodecyl. Preferably, $R_8$ is an alkyl group with 1 to 4 C atoms. However, the particularly preferred meaning of $R_8$ is hydrogen.

Examples of $R_8$ as $C_1-C_8$ alkyl are methyl, ethyl, isopropyl, n-butyl, amyl, n-hexyl or n-octyl. Alkyl groups with 1-4 C atoms, and especially ethyl and methyl, are preferred. Compounds in which $R_8$ denotes methyl are to be singled out in particular.

Examples of $R_9$ as $C_1-C_{12}$ alkyl are methyl, ethyl, n-propyl, n-butyl, n-pentyl, n-hexyl, n-octyl, n-decyl or n-dodecyl. Alkyl groups with 1-8 C atoms, in particular those with 1-4 C atoms and above all methyl, are preferred.

Examples of $R_9$ as $C_3-C_6$ alkenyl are allyl, 2-butenyl or 2-hexenyl, especially allyl.

An example of $R_9$ as $C_3-C_4$ alkinyl is propargyl.

If $R_9$ denotes $C_2-C_{21}$ alkoxyalkyl, the alkyl part can contain 1-3 C atoms and the alkoxy part can consist of 1-18 C atoms, such as, for example, in methoxymethyl, ethoxymethyl, 2-methoxyethyl, 2-ethoxyethyl, 2-n-butoxyethyl, 3-n-butoxyethyl, 2-octoxyethyl or 2-octadecyloxyethyl, and compounds in which $R_9$ denotes an alkoxy group with 2–6 C atoms should be especially mentioned.

Examples of $R_9$ as $C_7$–$C_9$ aralkyl are benzyl or α-phenylethyl.

Examples of $R_9$ as an aliphatic acyl group with 1–4 C atoms are formyl, acetyl, acryloyl or crotonyl, especially acety.

If $R_9$ is the group —CH$_2$COOR$_{10}$, $R_{10}$ as $C_1$–$C_{12}$ alkyl denotes, for example, methyl, ethyl, isopropyl, n-butyl, isobutyl, t-butyl, isopentyl, n-octyl, n-decyl or n-dodecyl. Preferably, $R_{10}$ is $C_1$–$C_4$ alkyl, and examples of $R_9$ as $C_3$–$C_6$ alkenyl are allyl, 2-butenyl or 2-hexenyl. Examples of $R_{10}$ as $C_7$–$C_8$ aralkyl are benzyl or α-phenylethyl.

If $R_9$ is the group —CH$_2$—CH(R$_{11}$)—OR$_{12}$, $R_{11}$ denotes hydrogen, methyl or phenyl, especially hydrogen. Examples of $R_{12}$ as an aliphatic, aromatic, alicyclic or araliphatic $C_1$–$C_{18}$ acyl radical which is substituted in the aromatic part, if appropriate, by chlorine, $C_1$–$C_4$ alkyl, such as methyl, ethyl, n-propyl or t-butyl, or by $C_1$-octanoyl, 8 alkoxy, such as methoxy, ethoxy, butoxy or octoxy, and/or by hydroxyl, are acetyl, propionyl, butyryl, octanoul, dodecanoyl, stearoyl, acryloyl, benzoyl, chlorobenzoyl, toluoyl, isopropylbenzoyl, 2,4-dichlorobenzoyl, 4-methoxybenzoyl, 3-butoxybenzoyl, 2-hydroxybenzoyl, 3,5-di-t-butyl-4-hydroxybenzoyl, β-(3,5-di-t-butyl-4-hydroxyphenyl)-propionyl, phenylacetyl, cinnamoyl or hexahydrobenzoyl.

If $R_9$ is the group —COOR$_{13}$, examples of $R_{13}$ as $C_1$–$C_{12}$ alkyl are methyl, ethyl, isobutyl, n-hexyl, n-octyl, n-decyl or n-dodecyl. Alkyl groups with 1–4 C atoms are preferred as $R_{13}$.

If $R_9$ is —CONHR$_{13}$, $R_{13}$ is especially cyclohexyl or phenyl.

Y is —O— or —NR$_{14}$, preferably —O—, and examples of $R_{14}$ as $C_1$–$C_{12}$ alkyl are methyl, ethyl, n-butyl, n-hexyl, n-octyl, n-decyl, or n-dodecyl.

Examples of $R_1$ as $C_1$–$C_{18}$ alkyl are methyl, ethyl, isopropyl, n-butyl, n-pentyl, n-hexyl, n-octyl, n-decyl, n-dodecyl, n-tetradecyl, n-hexdecyl or n-octadecyl.

Examples of $R_1$ as $C_5$–$C_7$ cycloalkyl are cyclopentyl, methylcyclopentyl, cyclohexyl or methylcyclophexyl and examples of $R_{15}$ as $C_1$–$C_{18}$ alkyl are methyl, ethyl, isopropyl, n-butyl, sec.-butyl, t-butyl, amyl, n-hexyl, n-octyl, n-decyl, n-dodecyl, n-tetradecyl, n-hexadecyl or n-octadecyl.

Examples of $R_{15}$ as $C_5$–$C_7$ cycloalkyl are cyclopentyl, methylcyclopentyl, cyclohexyl or methylcyclohexyl.

Examples of $R_{15}$ as $C_1$–$C_{18}$ alkoxy are straight-chain alkoxy with 1–6 C atoms, such as methoxy or ethoxy, and an example of $R_{15}$ as $C_5$–$C_7$ cycloalkoxy is especially cyclohexyloxy.

Examples of $R_{15}$ as $C_7$–$C_9$ aralkyl are benzyl, α-ethylphenyl or α,α-dimethylbenzyl.

Examples of $R_2$ as $C_1$–$C_{18}$ alkyl are methyl, ethyl, isopropyl, n-butyl, n-pentyl, n-hexyl, n-octyl, n-decyl, n-dodecyl, n-tetradecyl, n-hexadecyl or n-octadecyl.

Examples of $R_2$ as $C_5$–$C_7$ cycloalkyl are cyclopentyl, methylcyclopentyl, cyclohexyl or methylcyclohexyl, preferably cyclohexyl.

Examples of $R_2$ as $C_6$–$C_{10}$ aryl are phenyl, α-naphthyl or β-naphthyl, especially phenyl.

Examples of $R_2$ as $C_7$–$C_9$ aralkyl are benzyl, α-ethylphenyl, or α,α-dimethylbenzyl.

Salts which may be mentioned of the compounds, containing radicals of the formula III or V, are especially acid addition salts with inorganic or organic acids. The salts can be obtained in the customary manner and the free bases which in turn are preferred can be recovered from the salts. Acids which are suitable for forming salts are in particular inorganic acids, such as hydrochloric acid, sulphuric acid and phosphoric acid but also organic acids, such as, for example, p-toluenesulphonic acid.

Those compounds of the formula I are preferred, in which R denotes hydrogen or one of the groups of the formula II or III, wherein $R_3$ is hydrogen, $R_4$ denotes $C_1$–$C_{12}$ alkyl, $R_5$ is —OH, $R_6$ is hydrogen or $C_1$–$C_{12}$ alkyl, $R_7$ denotes hydrogen or $C_1$–$C_6$ alkyl, $R_8$ is hydrogen or $C_1$–$C_4$ alkyl and $R_9$ is hydrogen, oxyl, $C_1$–$C_8$ alkyl, $C_3$–$C_4$ alkenyl or alkinyl, $C_2$–$C_6$ alkoxyalkyl, $C_7$–$C_8$ aralkyl, acetyl, acryloyl or crotonyl or one of the groups —CH$_2$—COOR$_{10}$, —CH$_2$—CH(R$_{11}$)—OR$_{12}$, —COOR$_{13}$ or —CONHR$_{13}$, wherein $R_{10}$ is $C_1$–$C_4$ alkyl, $C_3$–$C_4$ alkenyl, phenyl, $C_7$–$C_8$ aralkyl or cyclohexyl, $R_{11}$ is hydrogen, methyl or phenyl, $R_{12}$ denotes hydrogen or an aliphatic, aromatic, alicyclic or araliphatic acryl group with 1–18 C atoms, wherein the aromatic part, if appropriate, can be substituted by chlorine, $C_1$–$C_4$ alkyl, $C_1$–$C_8$ alkoxy and/or hydroxyl, and $R_{13}$ is $C_1$–$C_{12}$ alkyl, X is —O— or —NR$_{14}$— wherein $R_{14}$ denotes hydrogen or $C_1$–$C_{12}$ alkyl, n denotes 1 to 5 and, if R is hydrogen or a group of the formula II, $R_1$ denotes $C_1$–$C_{18}$ alkyl, cyclohexyl, a group of the formula II or a group of the formula IV, wherein $R_{15}$ is $C_1$–$C_{18}$ alkyl, or is a group of the formula V and, if R is a group of the formula III, $R_1$ denotes a group of the formula II and, if R is hydrogen or a group of the formula II, $R_2$ denotes a group of the formula III or VI and, if R is a group of the formula III, $R_2$ denotes $C_1$–$C_{18}$ alkyl or one of the groups II, III or V.

Those compounds of the formula I are particularly preferred, in which R denotes hydrogen or a group of the formula II wherein $R_3$ denotes hydrogen, $R_4$ denotes $C_1$–$C_6$ alkyl, $R_5$ is —OH, $R_6$ denotes hydrogen or $C_1$–$C_6$ alkyl, $R_7$ denotes hydrogen or $C_1$–$C_4$ alkyl, $R_1$ denotes $C_1$–$C_{18}$ alkyl or a group of the formula II or a group of the formula IV, wherein $R_{15}$ is $C_1$–$C_{18}$ alkyl or a group of the formula V wherein $R_8$ denotes hydrogen, methyl or ethyl and $R_9$ is hydrogen, $C_1$–$C_4$ alkyl, allyl, propargyl, $C_2$–$C_6$ alkoxyalkyl, acetyl, acryloyl or crotonoyl or one of the groups —CH$_2$COOR$_{10}$, —CH$_2$—CH(R$_{11}$)—OR$_{12}$, —COOR$_{13}$ or —CONHR$_{13}$, wherein $R_{10}$ is $C_1$–$C_4$ alkyl, $R_{11}$ denotes hydrogen or methyl, $R_{12}$ denotes hydrogen and $R_{13}$ is $C_1$–$C_4$ alkyl, X is —O— or —NR$_{14}$— wherein $R_{14}$ is hydrogen or methyl, n denotes 1 to 3 and $R_2$ denotes one of the groups III or VI, wherein the radicals $R_8$, $R_9$, $R_{10}$, $R_{11}$, $R_{12}$, $R_{13}$ and $R_{14}$ have the meaning defined above.

Those compounds of the formula I are also important in which R denotes hydrogen or a group of the formula II wherein $R_3$ and $R_6$ are hydrogen, $R_4$ denotes $C_1$–$C_4$ alkyl, $R_5$ denotes —OH, $R_7$ denotes hydrogen or methyl, $R_1$ denotes a group of the formula II or IV, wherein $R_{15}$ is a group of the formula V wherein $R_8$ is hydrogen and $R_9$ is hydrogen, methyl or acetyl, and X denotes —O— or —NH—, n is 1 to 3 and $R_2$ denotes one of the groups III or VI, wherein the radicals $R_8$ and $R_9$ have the meaning defined above.

Compounds which are of great interest and which have a particularly good action are those wherein n denotes 1.

Examples of compounds of the formula I are: 1,3-di[(2,2,6,6-tetramethyl-piperidin-4-yl-oxy)-carbonyl-methyl]-barbituric acid, 5,5-di-[2-(2,2,6,6-tetramethyl-piperidin-4-yl-oxy)-carbonylethyl]-barbituric acid, 1,3-di-[3,5-di-t.butyl-4-hydroxy-benzyl]-5,5-di-[2-(1,2,2,6,6-pentamethyl-piperidin-4-yl-oxy)-carbonyl-n-propyl]-barbituric acid, 5,5-di-(2,2,6,6-tetramethyl-N-acetyl-piperidin-4-yl-oxy)-barbituric acid, 1,3-di-[3-methyl-5-t.butyl-4-hydroxybenzyl]-5-[(2,2,6,6-tetramethyl-piperidin-4-yl-imino)-carbonylethyl]-barbituric acid, 5,5-di-[(2,2,6,6-tetramethyl-N-acetyl-piperidin-4-yl-imino)-carbonylmethyl]-barbituric acid, 1,3,5-tris-[2(1,2,2,6,6-pentamethylpiperidin-4-yl-oxy)-carbonylethyl]-barbituric acid, 1,3-di-[3,5-di-t.butyl-4-hydroxybenzyl]-5,5-di-[(2,2,6,6-tetramethylpiperidin-4-yl-oxy)-carbonylmethyl]-barbituric acid, 1,3,5-tris-[3,5-di-t.butyl-4-hydroxybenzyl]-5-[2-(2,2,6,6-tetramethyl-piperidin-4-yl-oxy)-carbonylpropyl]-barbituric acid, 1,3,5-tris-[2,6-dimethyl-4-t.butyl-3-hydroxybenzyl]-5-[(2,2,6,6-tetramethyl-piperidin-4-yl]-barbituric acid, 1,3,5-tris-[2-(2,2,6,6-tetramethyl-piperidin-4-yl-oxy)-carbonylethyl]-5-[3,5-di-t.butyl-4-hydroxybenzyl]-barbituric acid, 1,3di-[2,3,6-trimethyl-2,6-diethyl-piperidin-4-yl-imino)-carbonylmethyl]-5-octyl-5-(3,5-di-t.butyl-4-hydroxybenzyl)-barbituric acid and 1,3,5,5-tetra-[2-(2,2,6,6-tetramethyl-piperidin-4-yl-oxy)-carbonylethyl]-barbituric acid.

The compounds of the formula I can be manufactured by various methods which are in themselves known.

In the simplest manner, they are manufactured by classical esterification or amidisation reactions wherein a compound of the formula VII

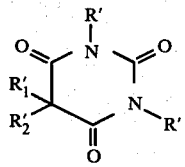 (VII)

in which at least one of the radicals R', $R_1'$ and $R_2'$ denotes a group of the formula VIII

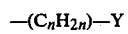 (VIII)

in which Y denotes one of the groups —$COOR_{16}$, —COhal or —CN, in which $R_{16}$ denotes hydrogen or preferably $C_1$-$C_4$ alkyl and hal is chloride, bromide or iodide, and the other of radicals R', $R_1'$ and $R_2'$ have the meaning of R, $R_1$ and $R_2$, is reacted with a compound of the formula IX

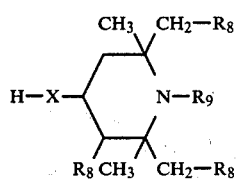 (IX).

To prepare a compound of the formula VII, an ester functional group is introduced into the barbituric acid ring, for example by reacting barbituric acid or a derivative thereof with a halide of the formula VIIIa

 (VIIIa).

The ester functional groups in the 5-position are preferably introduced before the cyclisation. This variant is described further below.

Compounds of the formula VII in which R' denotes hydrogen are most readily accessible.

Compounds of the formula I in which $R_2$ denotes a radical of the formula VI can be prepared in a manner which is in itself known by reacting a malonate of the formula X

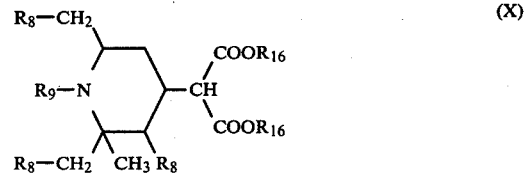 (X)

wherein the symbols have the meaning defined above, with urea in the presence of a strong base, such as an alcoholate, for example sodium ethanolate. The barbituric acid derivative, thus formed, of the formula XI

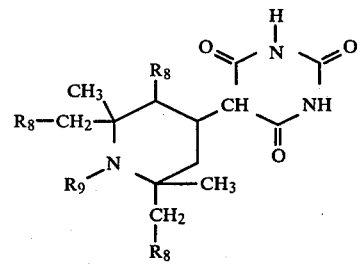 (XI)

can be subjected to further substitution reactions, such as are described further below.

A group of the formula III can be introduced before or after cyclisation, for example by reacting a compound of the formula XII

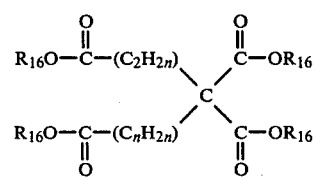 (XII)

with urea in the presence of a strong base, in order to close the barbituric acid ring, and subsequently reacting the barbituric acid derivative formed with a compound of the formula IX.

However, it is also possible to react a compound of the formula XIII

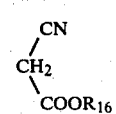 (XIII)

with a 4-oxopiperidine of the formula XIV

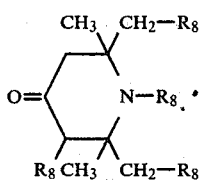

(XIV)

and subsequently to pass in hydrogen, a compound of the formula XV

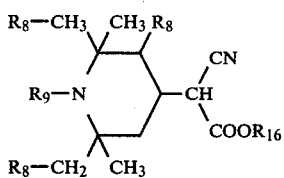

(XV)

being formed. The nitrile of the formula XV can be esterified in a known manner and the resulting diester can be reacted with urea to give the corresponding barbituric acid derivative.

In the simplest manner, the groups of the formula II are introduced by reacting a compound of the formula VIIa

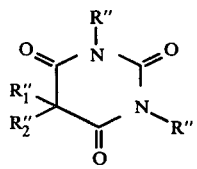

(VIIa)

in which at least one of the radical R'', $R_1''$ and $R_2''$ denotes hydrogen and the other radicals have the meaning of R, $R_1$ and $R_2$, with a Mannich base of the formula XVI

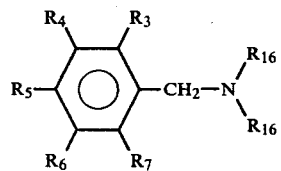

(XVI)

or with a dithiocarbamate of the formula XVII

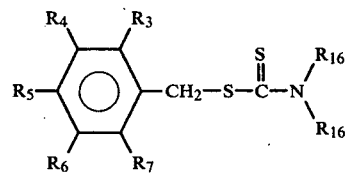

(XVII).

The phenolic radicals can be introduced before or after the introduction of the piperidine radicals, a subsequent introduction being simplest.

The phenols of the formula XVI and XVII are known compounds.

The piperidines of the formula IX are known, for example 4-hydroxy-piperidines are known from DT-OS No. 2,352,658 and 4-amino-piperidines are known from U.S. Pat. No. 3,684,765. In general, the 4-OH compounds can be manufactured from the corresponding 4-oxopiperidines of the formula XIV by reduction, for example by catalytic hydrogenation over Raney nickel, whilst the 4-NH$_2$ compounds are obtainable from the 4-oxopiperidines of the formula XIV, for example by means of a reductive conversion with ammonia.

The 4-oxopiperidines of the formula XIV in which $R_9$ is hydrogen, can be manufactured by various processes.

Thus, for example, W. Traube in Chem. Ber. 41, 777 (1908) describes the reaction of an aliphatic ketone with ammonia.

4-Oxopiperidines of the formula XIV in which $R_9$ denotes hydrogen, can also be manufactured analogously to the process described in U.S. Pat. No. 3,513,170. Here, an alkyl-substituted tetrahydropyrimidine is hydrolytically rearranged in the presence of an acid catalyst.

N-H compounds of the formula XIV which carry different substituents in the 2-position and 6-position, can be manufactured by reacting a ketone of the formula CH$_3$—CO—CH$_2$—R$_8$ with ammonia. The pyrimidine formed is hydrolysed, as described in Helv. Chem. Acta 30, 114 (1947), to give an aminoketone of the formula XVIII.

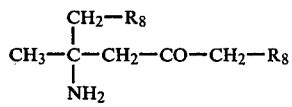

(XVIII)

Compounds of the formula XVIII are reacted, in a second process step, with ammonia and a ketone CH$_3$—CO—CH$_2$—R$_8$, as is described, for example, in Monatsh. Chemie 88, 464 (1957). The compounds of the formula VII in which $R_9$ denotes hydrogen, can be obtained from the resulting pyrimidine by hydrolysis.

Compounds of the formula XIV, in which $R_9$ does not denote hydrogen, can be manufactured from the corresponding N—H compounds by substitution. This step involves the substitution reactions customary for secondary amines, although these reactions proceed more slowly because of the steric hindrance by the methyl group or the group —CH$_2$—R$_8$. For example, the N—H compounds can be reacted with alkyl, alkenyl, aralkyl or alkoxyalkyl halides, dialkyl sulphates, epichlorohydrins, esters of chlorocarboxylic acids, such as esters of chloroacetic acid, or acid chlorides or acid anhydrides.

The group —CH$_2$—CH(R$_{11}$)—OR$_{12}$ can be introduced by reacting the N-H-piperidines with an epoxide of the formula

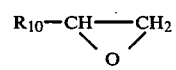

and subsequently acylating the product with an acyl chloride of the formula R$_{12}$Cl.

Compounds of the type of 2,2,6,6-tetramethyl-4-(carbalkoxycyanomethyl)-piperidine, which can be used as intermediate products, are moreover known from British Pat. No. 1,214,426.

According to the present invention, the compounds of the formula I can be used as stabilisers for plastics against damage thereto by the action of oxygen, heat and light.

The good light stabilising properties of the new compounds should be particularly singled out. All the compounds of the formula I which contain a radical of the formula II, also display, furthermore, a good anti-oxidative activity. The coupled protective effects are industrially useful and have the advantage that the frequently adverse side affects which occur on physical mixing of different stabilisers, disappear.

Examples of plastics which can be stabilised with the new compounds are listed in DT-OS No. 2,456,864 on pages 12–14.

The stabilisation of polyolefins, styrene polymers and polyurethanes is of particular importance and the compounds of the formula I are outstandingly suitable for this purpose. Examples of these are polyethylene of high and low density, polypropylene, ethylene/propylene copolymers, polystyrene, styrene/butadiene/acrylonitrile copolymers, mixtures of polyolefines or of styrene polymers, polyurethanes, based on polyethers or polyesters, in the form of films, lacquers, elastomers or foams. The compounds of the formula I are particularly suitable for stabilising ABS.

The stabilisers are added to the plastics in a concentration of 0.01 to 5% by weight, calculated on the material to be stabilised. Preferably 0.03 to 1.5, particularly preferably 0.2 to 0.6, % by weight of the compounds, calculated on the material to be stabilised, are incorporated into the latter.

The incorporation can be carried out after the polymerisation, for example by admixing the compounds and, optionally, further additives to the melt by the methods customary in the art, before or during shaping, or by applying the dissolved or dispersed compounds to the polymer, if appropriate with subsequent evaporation of the solvent.

The new compounds can also be added to the plastics to be stabilised in the form of a master batch which contains these compounds, for example in a concentration of 2.5 to 25% by weight.

In the case of crosslinked polyethylene, the compounds are added before crosslinking.

The invention thus also relates to the plastics which have been stabilised by the addition of 0.01 to 5% by weight of a compound of the formula I and which optionally can also contain further known and customary additives. The plastics stabilised in this way can be used in very diverse forms, for example as films, fibres, tapes, profiles or as binders for lacquers, adhesives or cements.

Examples which may be mentioned of further additives which can be employed together with the stabilisers to be used according to the invention are: antioxidants, such as simple 2,6-dialkylphenols, derivatives of alkylated hydroquinones, hydroxylated thiodiphenyl ethers, alkylidene-bisphenols, O-, N- and S-benzyl compounds, hydroxybenzylated malonates, hydroxybenzyl-aromatic compounds, s-triazine compounds, amides of β-(3,5-di-tert,-butyl-4-hydroxyphenyl)-propionic acid, esters of β-(3,5-di-tert.-butyl-4-hydroxyphenyl)-propionic acid, esters of β-(5-tert.-butyl-4-hydroxy-3-methylphenyl)-propionic acid, esters of 3,5-di-tert.-butyl-4-hydroxyphenylacetic acid, acylaminophenols, benzyl-phosphonates and aminoaryl derivatives, UV absorbers and light stabilisers, such as 2-(2'-hydroxyphenyl)-benztriazoles, 2,4-bis-(2'-hydroxyphenyl)-6-alkyl-s-triazines, 2-hydroxybenzophenones, 1,3-bis-(2'-hydroxybenzoyl)-benzenes, esters of optionally substituted benzoic acids and acrylates, and furthermore nickel compounds, sterically hindered amines, oxalic acid diamides, metal deactivators, phosphites, compounds which destroy peroxides, polyamide stabilisers, basic co-stabilisers, PVC stabilisers, nucleating agents or other additives, such as, for example, plasticisers, lubricants, emulsifiers, fillers, carbon black, asbestos, kaolin, talc, glass fibres, pigments, optical brighteners, flameproofing agents and antistatic agents.

Examples of further additives which can be employed together with the stabilisers to be used according to the invention can be found in DT-OS No. 2,427,853 on pages 18–24.

The following Examples further illustrate the present invention.

EXAMPLE 1

10 g (0.036 mol) of 5-(2,2,6,6-tetramethyl-4-piperidinyl)barbituric acid and 28.6 g (0.11 mol) of N-(3,5-di-tert.-butyl-4-hydroxybenzyl)-dimethyl-amine are dissolved in 150 ml of dimethylformamide and stirred for 15 hours at 140° C. The reaction mixture is poured into ice water; the precipitate is filtered off with suction and recrystallised from acetonitrile. The resulting 1,3,5-tris-(3,5-di-tert.-butyl-4-hydroxybenzyl)-5-(2,2,6,6-tetramethyl-4-piperidinyl)-barbituric acid has a melting point of 235° C. (stabiliser 1).

EXAMPLE 2

11.2 g (0.05 mol) of 5-(carbomethoxy-2-methyl-ethyl)-barbituric acid and 39.6 g of N-(3,5-di-tert.-butyl-4-hydroxybenzyl)-dimethylamine are dissolved in 150 ml of dimethylformamide and stirred for 15 hours at 140° C. The reaction mixture is poured into ice water; the precipitate is filtered off with suction and recrystallised from acetonitrile. The resulting 1,3,5-tris-(3,5-di-tert.-butyl-4-hydroxybenzyl)-5-(carbomethoxy-2-methylethyl)-barbituric acid has a melting point of 215° C. (stabiliser 2a).

13.2 g (0.015 mol) of the compound 2a and 2.6 g (0.015 mol) of 1,2,2,6,6-pentamethyl-4-hydroxy-piperidine are dissolved in 20 ml of xylene, and the solution is heated to 125° C. There is added 1 g of tetrabutylorthotitanate, and the temperature is then maintained at 135°–140° C. for 4 hours. The residual methanol and xylene is evaporated off in vacuo at the above temperature. The residue is recrystallised directly from ligroin. The 5-[(1,2,2,6,6-pentamethyl-4-piperidinyloxycarbonyl)-2-methyl-ethyl)]-1,3,5-tris-( 3,5-di-tert.-butyl-4-hydroxybenzyl)-barbituric acid thus obtained has a melting point of 138° C. (stabiliser 2).

What is claimed is:

1. A compound of the formula I

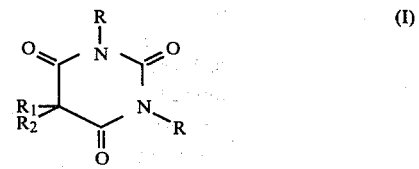

in which R is hydrogen or one of the groups

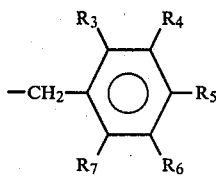  (II)

or

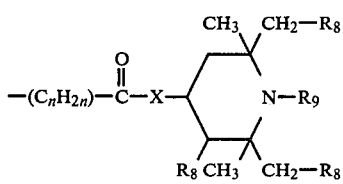  (III)

or an addition salt of formula III, wherein one of $R_3$ and $R_5$ is —OH and the other is hydrogen, $R_4$ denotes $C_1$-$C_{12}$ alkyl, $C_5$-$C_7$ cycloalkyl, phenyl, α-naphthyl, β-naphthyl or $C_7$-$C_9$ aralkyl, $R_6$ and $R_7$ are hydrogen, $C_1$-$C_{12}$ alkyl, $C_5$-$C_7$ cycloalkyl, phenyl, α-naphthyl, β-naphthyl or $C_7$-$C_9$ aralkyl, $R_8$ is hydrogen or $C_1$-$C_8$ alkyl and $R_9$ is hydrogen, oxyl, $C_1$-$C_{12}$ alkyl, $C_3$-$C_6$ alkenyl, $C_3$-$C_4$ alkinyl, $C_2$-$C_{21}$ alkoxyalkyl, $C_7$-$C_8$ aralkyl, 2,3-epoxypropyl, an aliphatic acyl group of a carboxylic acid with 1-4 C atoms, or one of the groups —$CH_2COOR_{10}$, —$CH_2$—$CH(R_{11})$—$OR_{12}$, —$COOR_{13}$ or —$CONHR_{13}$, wherein $R_{10}$ is $C_1$-$C_{14}$ alkyl, $C_3$-$C_6$ alkenyl, phenyl, $C_7$-$C_8$ aralkyl or cyclohexyl, $R_{11}$ is hydrogen, methyl or phenyl, $R_{12}$ denotes hydrogen, benzoyl, an aliphatic, phenylaliphatic or alicyclic acyl group of a carboxylic acid with 1-18 C atoms, wherein the phenyl moiety of the benzoyl and phenylaliphatic acyl groups can optionally be substituted by one or two chlorine atoms, one or two $C_1$-$C_4$ alkyl groups or one $C_1$-$C_8$ alkoxy group, and/or substituted by one hydroxyl group, and $R_{13}$ denotes $C_1$-$C_{12}$ alkyl, cyclohexyl, phenyl or benzyl, X is —O— or —$NR_{14}$— wherein $R_{14}$ denotes hydrogen or $C_1$-$C_{12}$ alkyl, and n denotes 1 to 5, and, if R is hydrogen or a group of formula II, $R_1$ denotes hydrogen, $C_1$-$C_{18}$ alkyl, $C_5$-$C_7$ cycloalkyl, a group of the formula II or a group of the formula $R_{15}$—CO—$(C_nH_{2n})$— (IV) wherein n has the meaning defined above and $R_{15}$ denotes $C_1$-$C_{18}$ alkyl, $C_5$-$C_7$ cycloalkyl, $C_1$-$C_{18}$ alkoxy, $C_5$-$C_7$ cycloalkoxy, $C_7$-$C_9$ aralkyl or a group of the formula

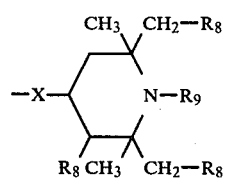  (V)

or an addition salt of formula V, wherein X, $R_8$ and $R_9$ have the meaning defined above, and, if R is a group of the formula III, $R_1$ denotes hydrogen or a group of the formula II, and, if R is hydrogen or a group of the formula II, $R_2$ denotes a group of the formula III or VI

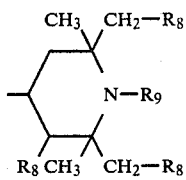  (VI)

wherein $R_8$ and $R_9$ have the meaning defined above, and, if R is a group of the formula III, $R_2$ denotes hydrogen, $C_1$-$C_{18}$ alkyl, $C_5$-$C_7$ cycloalkyl, phenyl, α-naphthyl, β-naphthyl, $C_7$-$C_9$ aralkyl or one of the groups II, III or V, with the proviso that said compound of formula I contains at least one phenolic moiety of the formula II and at least one hindered amine moiety selected from the group consisting of formula III, and addition salt of formula III, formula V, an addition salt of formula V, and formula VI.

2. A compound, according to claim 1, of the formula I in which R denotes hydrogen or one of the groups of the formula II or III, wherein $R_3$ is hydrogen, $R_4$ denotes $C_1$-$C_{12}$ alkyl, $R_5$ is —OH, $R_6$ is hydrogen or $C_1$-$C_{12}$ alkyl, $R_7$ denotes hydrogen or $C_1$-$C_6$ alkyl, $R_8$ is hydrogen or $C_1$-$C_4$ alkyl and $R_9$ is hydrogen, oxyl, $C_1$-$C_8$ alkyl, $C_3$-$C_4$ alkenyl, $C_3$-$C_4$ alkinyl, $C_2$-$C_6$ alkoxyalkyl, $C_7$-$C_8$ aralkyl, acetyl, acryloyl, crotonoyl or one of the groups —$CH_2$—$COOR_{10}$, —$CH_2$—$CH(R_{11})$—$OR_{12}$, —$COOR_{13}$ or —$CONHR_{13}$, wherein $R_{10}$ is $C_1$-$C_4$ alkyl, $C_3$-$C_4$ alkenyl, phenyl, $C_7$-$C_8$ aralkyl or cyclohexyl, $R_{11}$ is hydrogen, methyl or phenyl, $R_{12}$ denotes hydrogen, benzoyl, an aliphatic, phenylaliphatic or alicyclic acyl group of a carboxylic acid with 1-18 C atoms, wherein the phenyl moiety of the benzoyl and phenylaliphatic acyl groups can optionally be substituted by one or two chlorine atoms, one or two $C_1$-$C_4$ alkyl groups or one $C_1$-$C_8$ alkoxy group, and/or substituted by one hydroxyl group, and $R_{13}$ is $C_1$-$C_{12}$ alkyl, X is —O— or —$NR_{14}$— wherein $R_{14}$ denotes hydrogen or $C_1$-$C_{12}$ alkyl, n denotes 1 to 5 and, if R is hydrogen or a group of the formula II, $R_1$ denotes $C_1$-$C_{18}$ alkyl, cyclohexyl, a group of the formula II or a group of the formula IV, wherein $R_{15}$ is $C_1$-$C_{18}$ alkyl, or is a group of the formula V and, if R is a group of the formula III, $R_1$ denotes a group of the formula II and, if R is hydrogen or a group of the formula II, $R_2$ denotes a group of the formula III or VI and, if R is a group of the formula III, $R_2$ denotes $C_1$-$C_{18}$ alkyl or one of the groups II, III or V.

3. A compound, according to claim 1, of the formula I in which R denotes hydrogen or a group of the formula II wherein $R_3$ denotes hydrogen, $R_4$ denotes $C_1$-$C_6$ alkyl, $R_5$ is —OH, $R_6$ denotes hydrogen or $C_1$-$C_6$ alkyl, $R_7$ denotes hydrogen or $C_1$-$C_4$ alkyl, $R_1$ denotes $C_1$-$C_{18}$ alkyl, a group of the formula II or a group of the formula IV, wherein $R_{15}$ is $C_1$-$C_{18}$ alkyl or a group of the formula V wherein $R_8$ denotes hydrogen, methyl or ethyl and $R_9$ is hydrogen, $C_1$-$C_4$ alkyl, allyl, propargyl, $C_2$-$C_6$ alkoxyalkyl, acetyl, acryloyl, crotonyl or one of the groups —$CH_2$—$COOR_{10}$, —$CH_2$—$CH(R_{11})$—$OR_{12}$, —$COOR_{13}$ or —$CONHR_{13}$, wherein $R_{10}$ is $C_1$-$C_4$ alkyl, $R_{11}$ denotes hydrogen or methyl, $R_{12}$ denotes hydrogen and $R_{13}$ is $C_1$-$C_4$ alkyl, X is —O— or —$NR_{14}$— wherein $R_{14}$ is hydrogen or methyl, n denotes 1 to 3 and $R_2$ denotes one of the groups III or VI, wherein the radicals $R_8$, $R_9$, $R_{10}$, $R_{11}$, $R_{12}$, $R_{13}$ and $R_{14}$ have the meaning defined above.

4. A compound, according to claim 1, of the formula I in which R denotes hydrogen or a group of the formula II wherein $R_3$ and $R_6$ are hydrogen, $R_4$ denotes $C_1$–$C_4$ alkyl, $R_5$ denotes —OH, $R_7$ denotes hydrogen or methyl, $R_1$ denotes a group of the formula II or IV, wherein $R_{15}$ is a group of the formula V wherein $R_8$ is hydrogen and $R_9$ is hydrogen, methyl or acetyl, and X denotes —O— or —NH—, n is 1 to 3 and $R_2$ denotes one of the groups III or VI, wherein the radicals $R_8$ and $R_9$ have the meaning defined above.

5. A compound, according to claim 1, of the formula I wherein n denotes 1.

6. A composition comprising a plastic and a compound of the formula I according to claim 1, in an amount which is effective to stabilize said plastic against degradation by oxygen, heat or light.

7. A method of stabilizing a plastic against degradation by oxygen, heat or light, which comprises incorporating in said plastic a compound of the formula I according to claim 1, in an amount which is effective to stabilize said plastic against degradation by oxygen, heat or light.

8. A compound according to claim 1, which is selected from the group consisting of 1,3-di-[3,5-di-t.butyl-4-hydroxy-benzyl]-5,5-di-[2-(1,2,2,6,6-pentamethyl-piperidin-4-yl-oxy)-carbonyl-n-propyl]-barbituric acid, 1,3-di-[3-methyl-5-t.butyl-4-hydroxybenzyl]-5-[(2,2,6,6-tetramethyl-piperidin-4-yl-imino)-carbonylethyl]-barbituric acid, 1,3-di-[3,5-di-t.butyl-4-hydroxybenzyl]-5,5-di-[(2,2,6,6-tetramethyl-piperidin-4-yl-oxy)-carbonyolmethyl]-barbituric acid, 1,3,5-tris-[3,5-di-t.butyl-4-hydroxybenzyl]-5-[2-(2,2,6,6-tetramethyl-piperidin-4-yl-oxy)-carbonylpropyl]-barbituric acid, 1,3,5-tris-[2,6-dimethyl-4-t.butyl-3-hydroxybenzyl]-5-[(2,2,6,6-tetramethylpiperidin-4-yl]-barbituric acid, 1,3,5-tris-[2-(2,2,6,6-tetramethylpiperidin-4-yl-oxy)-carbonylethyl]-5-[3,5-di-t.butyl-4-hydroxybenzyl]-barbituric acid, and 1,3-di-[2,3,6-trimethyl-2,6-diethylpiperidin-4-yl-imino)-carbonylmethyl]-5-octyl-5-(3,5-di-t.butyl-4-hydroxybenzyl)-barbituric acid.

9. A composition according to claim 6, containing 0.01 to 5% by weight of the compound of formula I, based on the weight of the plastic.

10. A composition according to claim 6, wherein the plastic is a polyolefine, a styrene polymer or a polyurethane.

* * * * *